*(12)* United States Patent
Ehr et al.

(10) Patent No.: US 8,668,650 B2
(45) Date of Patent: Mar. 11, 2014

(54) PRESSURE-SENSING GUIDEWIRE AND SHEATH

(75) Inventors: Timothy G. J. Ehr, Elk River, MN (US); Bruce Howard Asmus, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2711 days.

(21) Appl. No.: 10/027,154

(22) Filed: Dec. 20, 2001

(65) Prior Publication Data

US 2003/0120175 A1 Jun. 26, 2003

(51) Int. Cl.
*A61B 5/02* (2006.01)
*A61B 5/00* (2006.01)

(52) U.S. Cl.
USPC .......................................... 600/486; 600/561

(58) Field of Classification Search
USPC ............. 600/485, 486, 488, 561; 604/164.01, 604/43, 171; 73/700
See application file for complete search history.

(56) References Cited

U.S. PATENT DOCUMENTS

| | | | |
|---|---|---|---|
| 4,168,703 A * | 9/1979 | Kenigsberg .................... | 600/561 |
| 4,621,646 A | 11/1986 | Bryant | |
| 4,846,191 A * | 7/1989 | Brockway et al. ............ | 600/561 |
| 4,924,877 A | 5/1990 | Brooks | |
| 4,953,553 A | 9/1990 | Tremulis | |
| 5,025,786 A | 6/1991 | Siegel | |
| 5,396,897 A * | 3/1995 | Jain et al. ...................... | 600/561 |
| 5,450,853 A | 9/1995 | Hastings et al. | |
| 5,706,826 A | 1/1998 | Schwager | |
| 5,836,885 A | 11/1998 | Schwager | |
| 5,916,177 A | 6/1999 | Schwager | |
| 5,919,188 A * | 7/1999 | Shearon et al. ................ | 606/41 |

(Continued)

FOREIGN PATENT DOCUMENTS

| | | |
|---|---|---|
| EP | 0388113 A2 | 3/1990 |
| NL | 1005134 | 8/1998 |
| WO | WO-99/56612 | 11/1999 |
| WO | WO-01/13789 A1 | 3/2001 |

OTHER PUBLICATIONS

Martini et al., "Fundamentals of Anatomy and Physiology". Prentice Hall, Englewwod Cliffs, New Jersey. 1995, p. 892.*

*Primary Examiner* — Max Hindenburg
*Assistant Examiner* — Jonathan M Foreman
(74) *Attorney, Agent, or Firm* — Seager, Tufte & Wickhem LLC

(57) ABSTRACT

A pressure sensing device is provided that can monitor and measure pressure at two points in a vessel or artery without moving the outer sheath or catheter of the device. The outer sheath or catheter includes two spaced apart openings that may be positioned in a vessel or artery on opposing sides of an occlusion. The device also includes an inner elongated tube with at least one opening. The inner elongated tube is slidable with respect to the outer sheath or catheter thereby permitting the opening of the elongated tube to be moved into selective registration with one of the openings of the outer sheath. A pressure measurement may be taken through one of the openings in the outer sheath by aligning the opening of the elongated tube with said opening and, then, a second pressure reading may be taken by sliding the elongated tube within the outer sheath so that the opening of the elongated tube is in registry with the other opening of the tubular sheath. As a result, pressure measurements at two points in a vessel or artery may be taken without moving the outer sheath or catheter.

5 Claims, 3 Drawing Sheets

(56) References Cited

U.S. PATENT DOCUMENTS

| | | |
|---|---|---|
| 5,964,714 A | 10/1999 | Lafontaine |
| 6,044,845 A | 4/2000 | Lewis |
| 6,077,230 A * | 6/2000 | Gregoire et al. .............. 600/566 |
| 6,183,424 B1 | 2/2001 | Schwager |
| 6,259,938 B1 * | 7/2001 | Zarychta et al. .............. 600/380 |
| 6,358,229 B1 * | 3/2002 | Tihon ....................... 604/170.03 |
| 2002/0049402 A1 * | 4/2002 | Peacock et al. .................... 604/8 |
| 2002/0065472 A1 * | 5/2002 | Brockway et al. ............ 600/486 |
| 2006/0106406 A1 * | 5/2006 | Weinberger ................... 606/153 |
| 2010/0305415 A1 * | 12/2010 | Rabinovitz et al. ........... 600/302 |
| 2012/0172781 A1 * | 7/2012 | Wang .......................... 604/6.16 |

\* cited by examiner

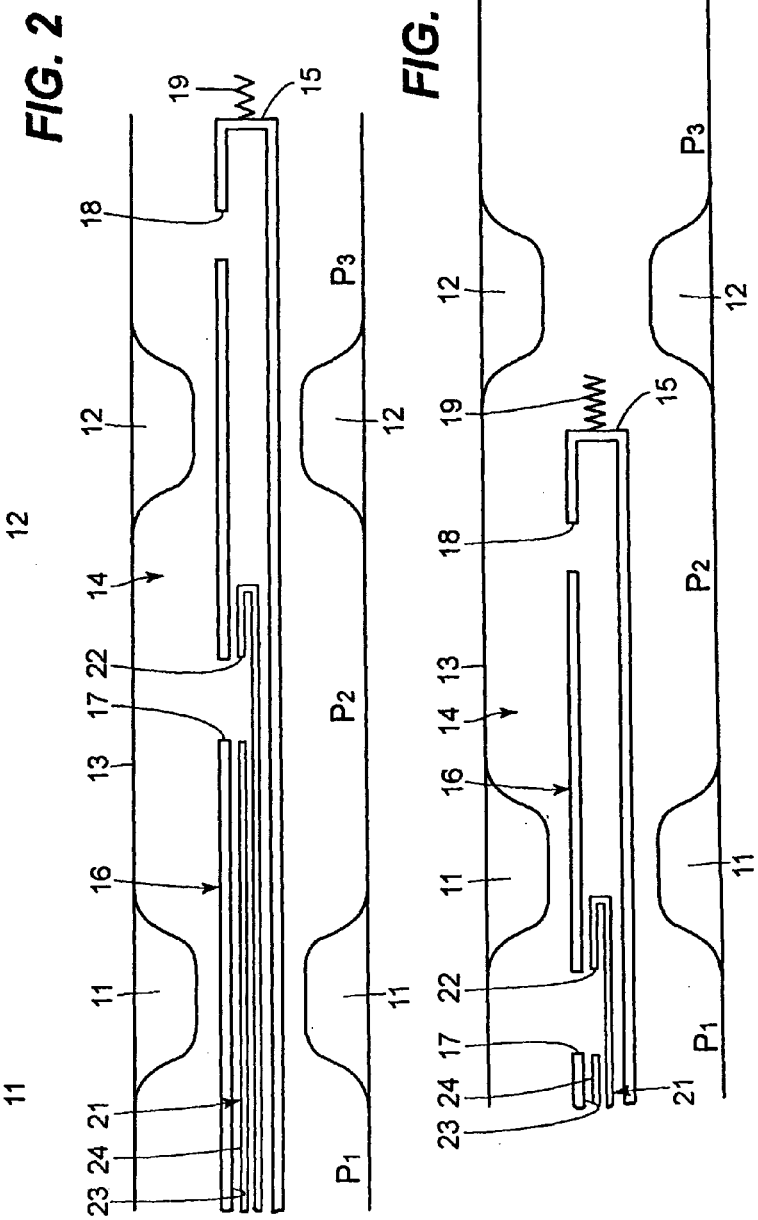

PRESSURE-SENSING GUIDEWIRE AND SHEATH

FIELD OF THE INVENTION

The present invention generally relates to intravascular medical devices and methods for monitoring and measuring fluid pressure. More specifically, the present invention relates to intravascular diagnostic devices and methods for monitoring and measuring fluid pressure at selected points in coronary vessels or arteries. Still more specifically, the present invention relates to intravascular devices and methods for monitoring and measuring fluid pressure at selected points in an artery on opposite sides of an occlusion or partial blockage. Those skilled in the art will recognize the benefits of applying the present invention to similar fields not discussed herein.

BACKGROUND OF THE INVENTION

Angioplasty procedures have gained wide acceptance in recent years as efficient and effective methods for treating many types of vascular disease. In particular, angioplasty is widely used for opening stenosis or occlusions in the coronary arteries, although it is also used for the treatment of stenosis in other parts of the vascular system.

The most widely used form of angioplasty makes use of a dilation catheter which has an inflatable balloon at its distal end. Inflation of the balloon at the site of the occlusion causes a widening of the vessel or artery to reestablish an acceptable blood flow through the vessel or artery.

It often is desirable to determine the severity of the occlusion in order to properly choose a dilation catheter or to make a determination as to whether treatment is required. Various techniques have been used to determine the severity of the occlusion. One way of determining the severity of the occlusion is to measure pressure both proximal to and distal of the occlusion.

Specifically, referring to FIG. 1 (which does not illustrate a prior art device, but which instead illustrates one disclosed embodiment), two occlusions 11, 12 are shown in an arterial wall 13. In determining the severity of the occlusion 11, knowledge of the ratio of the pressures $P_2:P_1$ is important. A ratio of $P_2:P_1$ of less than 0.75 is indicative of an occlusion requiring treatment and a ratio of $P_2:P_1$ of greater than 0.75 is indicative of an occlusion not requiring treatment. Similarly, with reference to the occlusion shown at 12 in FIG. 1, if the ratio $P_3:P_2$ is less than 0.75, it would be an indication that the occlusion 12 would require treatment. If the ratio $P_3:P_2$ is greater than 0.75, it would be an indication that the occlusion 12 does not require treatment.

Devices that are used for this purpose include catheter-like members with some type of pressure-sensing device incorporated therein. One known device measures the pressure as a function of the deflection of a diaphragm located at the proximal end of the catheter. One problem associated with currently available pressure-sensing devices is that they are unable to measure pressure at points both proximal and distal to the occlusion without moving the device. When the device or catheter is moved, it can often cause physical changes to the occlusion thereby affecting the second pressure measurement. Further, unnecessary movement of the catheter can dislodge a portion of the plaque that forms the occlusion. Further, because it is often difficult to insert catheters in coronary arteries and other vessels, physicians are often reluctant to move a catheter in a proximal direction once the catheter is in position. Hence, once a physician inserts a catheter past the point of occlusion, the physician is often reluctant to move the catheter to a point proximal to the occlusion to take a pressure measurement if a catheter must be moved back to a location distal to the occlusion at a later time in the procedure.

Accordingly, there is a need for an improved intravascular pressure-sensing device which can monitor and measure pressure at multiple points along a vessel or artery without moving the device. Still further, there is a need for an intravascular pressure-sensing device which can monitor and measure pressure at multiple points along a vessel or artery simultaneously.

It would be desirable to make use of both multi-point intravascular pressure sensing devices and methods in order to provide a physician with sufficient diagnostic information to make a determination as to whether the occlusion should be treated. The ideal multiple point pressure measurement device would be accurate, low profile, flexible and have a fast response time. Both the cost and ease of use of the complete system needs to be considered as well to produce a commercially successful product. Presently available devices are not capable of simultaneously meeting these various requirements.

SUMMARY OF THE DISCLOSURE

The present invention overcomes the deficiencies of the prior art by providing a pressure monitoring and measuring device that comprises an elongated tube having an opening. The elongated tube is slidably received in a tubular sheath. The tubular sheath comprises at least two spaced apart openings. The elongated tube is slidably within the tubular sheath thereby allowing the opening of the elongated tube to be selectively aligned with both openings of the tubular sheath. In use, the elongated tube is positioned within the tubular sheath so that its opening is aligned with one of the openings of the tubular sheath. A pressure measurement is made in this position. Then, the elongated tube is moved within the tubular sheath so that its opening is aligned with the other opening of the tubular sheath. A second pressure measurement is made in this position.

In use, the above described embodiment would be introduced into a patient's vasculature in advance to a point whereby one of the openings of the tubular sheath is disposed distal to an occlusion and the other of the openings in the tubular sheath is disposed proximal to the occlusion. In this way, the elongated tube can be manipulated to take a pressure reading at points both distal and proximal to the occlusion without moving the tubular sheath.

In another embodiment, a method for monitoring and measuring pressure on opposing sides of an occlusion is disclosed. The method comprises the steps of providing a pressure measuring device comprising an elongated tube having an opening. The elongated tube is slidably received in a tubular sheath. The tubular sheath comprises either at least two spaced apart openings or one elongated opening. The elongated tube has a proximal end connected to a pressure transducer. The method further includes the step of inserting the pressure measuring device into a vessel having an occlusion until one of the openings of the tubular sheath is disposed on one side of the occlusion and the other openings of the tubular sheath is disposed on an opposite side of the occlusion. The method further includes the steps of aligning the opening of the elongated tube with one of the openings of the tubular sheath or a portion of the elongated opening on one side of the occlusion, measuring the pressure at the one opening of the tubular sheath through the elongated tube, aligning the opening of the elongated tube with the other openings of the tubular sheath or a portion of the elongated opening on an opposite side of the occlusion, and measuring the pressure at the other opening of the tubular sheath through the elongated tube.

BRIEF DESCRIPTION OF THE DRAWINGS

FIG. 1 is a partial sectional schematic view illustrating a vessel or artery with two occlusions and the distal end of a disclosed pressure measuring device inserted into the vessel or artery and wherein the elongated tube of the pressure measuring device is in a first position to measure a pressure $P_3$ distal to the occlusion 12.

FIG. 2 is another partial sectional schematic view of the artery and device shown in FIG. 1 but with the elongated tube of the device moved to a second position to measure a pressure $P_2$ proximal to the occlusion 12 and distal to the occlusion 11.

FIG. 3 is another partial sectional schematic view of a vessel or artery and the device shown in FIG. 1 but with the device moved to a third position for measuring the pressure $P_1$ proximal to the occlusion 11.

DETAILED DESCRIPTION OF THE PRESENTLY PREFERRED EMBODIMENTS

Figure 4:
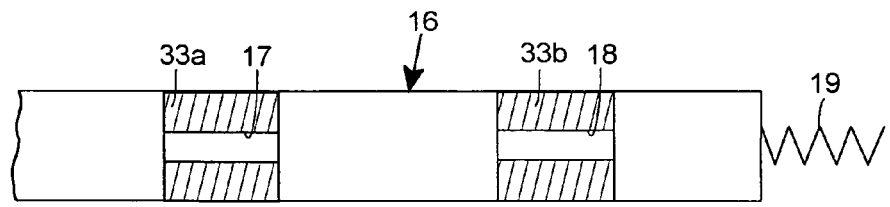
FIG. 4 is a partial elevational view of the tubular sheath of the pressure measuring device shown in FIG. 1.

Turning to FIG. 1, a vessel or artery 13 which includes occlusions 11 and 12. As discussed above, it is important for the physician to know the arterial pressure both proximal and distal to the occlusions 11 and 12 in order to make a determination as to whether the occlusions 11 and 12 require treatment. To make the determination with respect to the occlusion 12, the physician needs to know the pressures $P_2$ and $P_3$. In order to make a determination as to the occlusion 11, the physician needs to know the pressures $P_1$ and $P_2$.

Still referring to FIG. 1, a pressure measuring device 14 has been inserted into the vessel or artery 13 so that its distal end 15 is disposed past or distal to the occlusion 12. The device 14 includes an outer tubular sheath 16 having two openings 17, 18. The device 14 has been positioned in the vessel 13 so that the opening 17 is proximal to the occlusion 12 and the opening 18 is distal to the occlusion 12. A spring tip is shown schematically at 19. It will be understood that the spring tip 19 can be of a conventional type, two examples of which are shown and described in U.S. Pat. Nos. 5,964,714 and 5,860,938, both of which are assigned to the assignee of this application and which are incorporated herein by reference.

The device 14 further includes an elongated tube 21 that is slidably received within the tubular sheath 16. The elongated tube includes at least one opening 22. The elongated tube 21 can be moved with respect to the tubular sheath 16 so that the opening 22 of the elongated tube 21 can be moved from a position in substantial registry with the opening 18 of the tubular sheath 16 as shown in FIG. 1 to the position shown in FIG. 2 where the opening 22 of the elongated tube 21 is in substantial registry with the opening 17 of the tubular sheath 16. In the position shown at FIG. 1, the device 14 can measure the pressure $P_3$, i.e., the pressure distal to the occlusion 12. In a preferred embodiment, the elongated tube 21 is rotationally aligned with respect to the tubular sheath 16. In alternative embodiments, the elongated tube 21 may be slidably received within the tubular sheath 16, but fixed in a single position, for example, by way of a key and keyway, so they may not be rotatably moved relative to each other.

Figure 8:
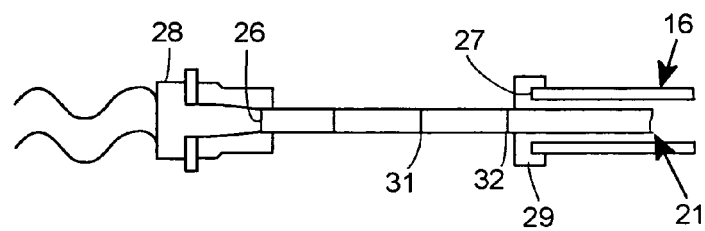
FIG. 8 is a partial sectional view of a proximal end of a disclosed pressure measuring device.

The device 14 can be manufactured so that the elongated tube 21 is frictionally received within the tubular sheath 16. That is, the device 14 can be constructed so that the inside surface 23 of the tubular sheath 16 engages the outside surface 24 of the elongated tube 21 so that fluid communication between the two surfaces is substantially prevented. If the device 14 is constructed in this way, a closed end for the tubular sheath 16 is not necessary. As shown in FIG. 8, the proximal end 26 of the elongated tube 21 extends outward from the proximal end 27 of the tubular sheath 16. The proximal end 26 of the elongated tube 21 is received in a pressure transducer 28. A seal 29 is provided at the proximal end 27 of the tubular sheath 16, which allows the elongated tube 21 to slide with respect to the tubular sheath 16 without allowing fluid to pass between the outside of the elongated tube 21 and the sheath 16.

Returning to FIG. 1, the device 14 is in a position where the pressure $P_3$ can be measured. Turning to FIG. 2, the elongated tube 21 has been shifted with respect to the tubular sheath 16 so that the opening 22 of the elongated tube 21 is now in registry with the opening 17 of the tubular sheath 16. In the position shown in FIG. 2, the pressure $P_2$ can be measured without moving the tubular sheath 16. For the embodiment illustrated in FIGS. 1-3, in order to measure the pressure $P_1$ proximal to the occlusion 11, the device 14 is moved laterally to the left or in a proximal direction so that either the opening 17 or opening 18 of the tubular sheath 16 is proximal to the occlusion 11 and the elongated tube 21 is shifted accordingly. As shown in FIG. 3, movement of the tubular sheath 16 is minimized and the opening 17 of the tubular sheath is moved to a position distal to the occlusion 11 and no shift of the elongated tube with respect to the tubular sheath 16 is necessary.

Figure 5:
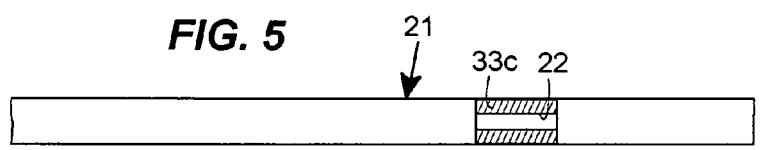
FIG. 5 is a partial elevational view of the elongated tube of the pressure measuring device shown in FIG. 1.

Turning to FIGS. 4, 5 and 8, it will be noted that the proximal end 26 of the elongated tube 21 may include a plurality of markings 31, 32 (see FIG. 8). Because the proximal end 26 of the elongated tube 21 extends outward from the proximal end 27 of the tubular sheath 16, the markings can be useful to the physician for lining up the opening 22 of the elongated tube 21 with the openings 17, 18 of the tubular sheath 16. In the examples shown in FIGS. 4, 5 and 8, a mark 32 can be provided at the proximal end 21 or at the seal 29 when the opening 22 of the elongated tube 21 is in registry with the opening 17 of the tubular sheath 16. Further, a second mark 31 can be provided that is aligned with the proximal end 27 of the tubular sheath 16 or seal 29 when the opening 22 of the elongated tube is in registry with the opening 18 of the tubular sheath 16. Other positioned indicators will be apparent to those skilled in the art.

Further, referring to FIGS. 4 and 5, radiopaque markers 33a, 33b and 33c may be provided in the form of a coil or band loaded into the sheath 16 or tube 21 which can viewed by positions using fluoroscopy.

Figure 6:
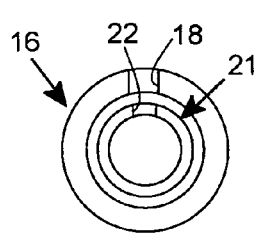
FIG. 6 is an end sectional view taken substantially along line 6-6 of FIG. 1.
Figure 7A:
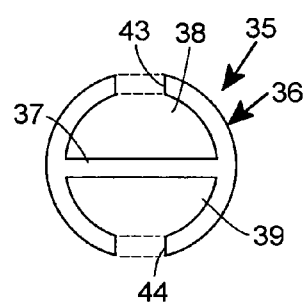
FIG. 7A is an end sectional view of an alternative pressure measuring device taken substantially along line 7A-7A of FIG. 7B
Figure 7B:
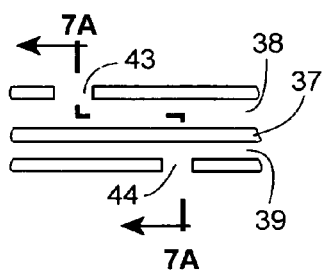
FIG. 7B is a partial side sectional view of the pressure measuring device shown in FIG. 7A.

Turning to FIGS. 6 and 7, it will be noted that a sectional view of the embodiment 14 shown in FIGS. 1-5 and 8 is shown in FIG. 6 while a sectional view of an alternative embodiment 35 is shown in FIG. 7. In the alternative embodiment 35, the tubular sheath 36 includes a wall 37 that extends along the length of the sheath 36 thereby creating two separate lumens 38, 39. An opening 43 in the sheath 36 is in alignment with the lumen 38 and an opening 44 is provided in the sheath 36 which is in alignment with the lumen 39. With the openings 43, 44 being laterally spaced apart, pressures at points proximal and distal to an occlusion can be measured simultaneously. That is, if the device 35 is positioned within a vessel or artery so that one of the openings 43 is proximal to an occlusion and the other of the openings 44 is distal to the occlusion, and two elongated tubes are provided in the position shown in FIG. 7, simultaneous pressure measurements at points both proximal and distal to the occlusion can be made.

Figure 9:
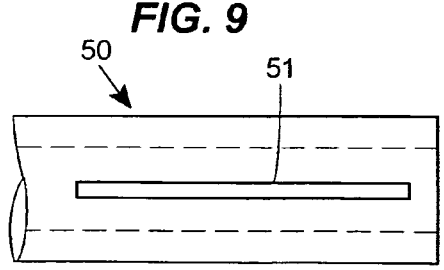
FIG. 9 is a partial elevational view of another alternative tubular sheath.
Figure 10:
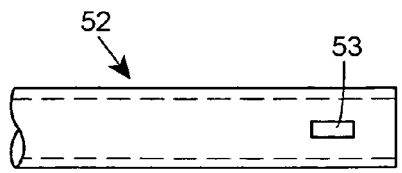
FIG. 10 is a partial elevational view of another elongated tube.

FIG. 9 is a partial view of a tubular sheath 50 with a single elongated slot or opening 51. The opening 51 is sufficiently long enough so that it can traverse a typical occlusion thereby leaving portions of the opening 51 at points both proximal and distal to the occlusion. An elongated tube 52 as shown in FIG. 10 is inserted into the sheath 50 and the small opening 53 can be moved to points proximal and distal to the occlusion for communicating a pressure reading through the opening 51.

Figure 11:
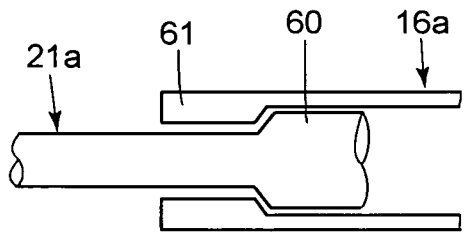
FIG. 11 is a partial sectional view illustrating a connection mechanism between the elongated tube and tubular sheath of one disclosed embodiment.
Figure 12:
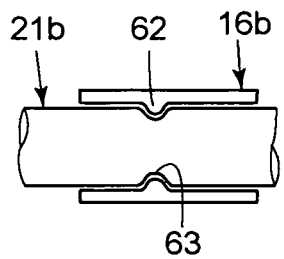
FIG. 12 is a partial sectional view illustrating a connection mechanism between the elongated tube and tubular sheath of another disclosed embodiment.
Figure 13:
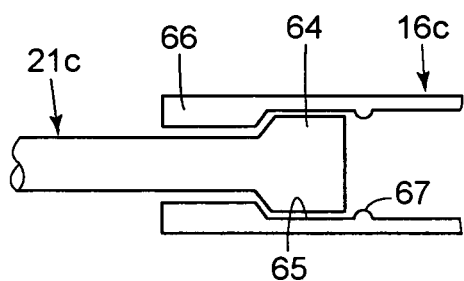
FIG. 13 is a partial sectional view illustrating a connection mechanism between the elongated tube and tubular sheath of yet another disclosed embodiment.
Figure 14:
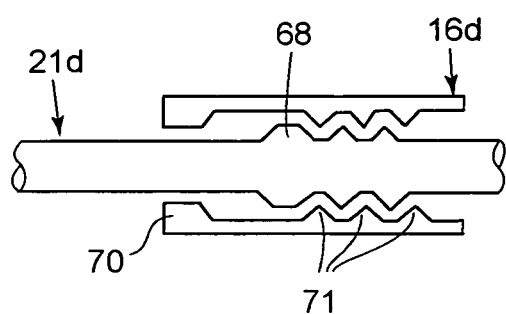
FIG. 14 is a partial sectional view illustrating a connection mechanism between the elongated tube and tubular sheath of another disclosed embodiment.

FIGS. 11-14 illustrate various mechanisms for connecting the elongated tubes 21a-21c to the tubular sheaths 16a-16d. In FIG. 11, the elongated tube 21a is equipped with a wedge portion 60 that is disposed distal to a radially inwardly extending section 61 of the tubular sheath 16a. The wedge 60 can be formed by grinding the tube 21a or additional material can be applied to the wedge section 60 such as a polymeric sleeve for purposes of enlarging the wedge section 60. In FIG. 12, a detent 62 is provided on the tubular sheath 16b which is received in a recess 63 in the elongated tube 21b. In FIG. 13, a similar wedge structure 64 is formed in the elongated tube 21c. The wedge 64 is received in a recess 65 in the tubular sheath 16c that is bound by a radially inwardly extending restricted portion 66 and a detent 67. In FIG. 14, a similar wedge structure 68 is provided on the elongated tube 21d and is disposed between a restricted portion 70 of the tubular sheath and complimentary threads 71, 72 disposed on the tubular sheath 16d and elongated tube 21d, respectively. The embodiments shown in FIGS. 11-13 are free to rotate with respect to each other while the threaded connection provided by the thread 71, 72 of FIG. 14 provide a more secure connection.

Both the sheath and tube of the disclosed pressure measuring devices can be made from a variety of materials, which will be apparent to those skilled in the art. The sheaths are preferably made from material suitable for the manufacture of pressure measuring guidewires. Such materials are commonly metallic, but it is anticipated that other polymeric materials may also be suitable for fabricating the sheath. The elongated tubes may also be made from metallic or polymer materials. Such suitable metallic or polymer materials include, but are not limited to polymer materials such as Pebax™, Arnitel™, polybutylene terephthalente (PBT), polyoxymethylene (POM), polyethylene (PE), polyethylene terephthalate (PET), polytetrafluoroethylene (PTFE), polyvinyl chloride (PVC), thermoplastic elastomer (TPE), polyamide and Nylon™ and metallic alloy materials such as Inconel 617™, Inconel 625™, Hastelloy S™, Hastelloy X™, Nimonic 90™, Incoloy 800™, MP35-N Elgiloy™, 304LV™, 316 LVM™, Aermet 100™, Aermet 310™, CRB-7™, Custom 450™, Custom 455™, Custom 465 m™, NiMark 250™, NiMark 250 NCO™, NiMark 300™, Nickel 200™, 304LV™, 316 LVM™, 321™, 347™, Aermet 100™, Aermet 310™, Haynes 214™, Haynes 230™, Inconel 600™, Inconel 601™, Inconel 617™, Inconel 625™, RA 333™, Hastelloy B™, Hastelloy N™, Hastelloy S™, Hastelloy W™, Hastelloy X™, Hastelloy C-276™, Haynes HR-120™, Haynes HR-160™, Nimonic 75™, Nimonic 86™, Haynes 556™, Incoloy 800™, Incoloy 800H™, Incoloy 800HT™, Incoloy 801™, Incoloy 802™, MP35-N™ and Elgiloy™ can be utilized.

While the specification describes preferred designs and methods, those skilled in the art will appreciate the spirit and scope of the invention with reference to the appended claims.

What is claimed:

1. A device for measuring blood pressure in a vascular structure, comprising:
   a tubular sheath sized for insertion into the vascular structure, the tubular sheath including an open proximal end, a closed distal end, at least two axially spaced apart openings in a sidewall thereof; and an inside peripheral surface,
   an elongated tube disposed within the tubular sheath and including an open proximal end, a closed distal end, a single opening in a sidewall thereof and an outside peripheral surface engaging the inside peripheral surface of the tubular sheath about the entire outside peripheral surface of the elongated tube,
   the elongated tube being frictionally received within the tubular sheath thereby allowing the opening of the elongated tube to be selectively aligned with one of the axially spaced apart openings of the tubular sheath at a time and so that engagement between the inside peripheral surface of the tubular sheath and the outside peripheral surface of the elongated tube substantially prevents fluid communication between the inside peripheral surface of the tubular sheath and the outside peripheral surface of the elongated tube and through the tubular sheath, and
   a pressure transducer in fluid communication with the elongated tube proximal end so that blood from the vascular structure is communicated to the pressure transducer when the elongated tube opening is aligned with one of the tubular sheath openings, thereby to directly measure the blood pressure;
   wherein the blood pressure measuring device has a distal portion that is
   inserted into the vascular structure, and wherein an exterior surface of the distal portion of the blood pressure measuring device has a cross-sectional profile of a single circle.

2. The pressure measuring device of claim 1 wherein the proximal end and the distal end of the tubular sheath define a first length,
   the proximal end and the distal end of the elongated tube define a second length, the second length being greater than the first length so that the proximal end of the elongated tube is disposed outside of the proximal end of the tubular sheath, the elongated tube further comprising two markings, one of the markings of the elongated tube being aligned with the proximal end of the tubular sheath when the opening of the elongated tube is aligned with one of the openings of the tubular sheath, the other of the markings of the elongated tube being aligned with the proximal end of the tubular sheath when the opening of the elongated tube is aligned with the other of the openings of the tubular sheath.

3. The pressure measuring device of claim 2 wherein at least one distal end of the tubular sheath or elongated tube comprises a radiopaque marker at a distal end thereof.

4. A device for measuring blood pressure in a vascular structure, comprising:

a tubular sheath sized for insertion into the vascular structure, the tubular sheath including an open proximal end, a closed distal end, and at least two axially spaced apart openings in a sidewall thereof, and an inside peripheral surface, an elongated tube disposed within the tubular sheath and including an open proximal end, a closed distal end and a single opening in a sidewall thereof; and an outside peripheral surface radially engaging the inside peripheral surface of the tubular sheath about the entire outside peripheral surface of the elongated tube, the elongated tube being slidable within the tubular sheath thereby allowing the opening of the elongated tube to be selectively aligned with one of the axially spaced apart openings of the tubular sheath at a time, the proximal end and the distal end of the tubular sheath define a first length, the proximal end and the distal end of the elongated tube define a second length, the second length being greater than the first length so that the proximal end of the elongated tube is disposed outside of the proximal end of the tubular sheath, the elongated tube further comprising two markings, one of the markings of the elongated tube being aligned with the proximal end of the tubular sheath when the opening of the elongated tube is aligned with one of the openings of the tubular sheath, the other of the markings of the elongated tube being aligned with the proximal end of the tubular sheath when the opening of the elongated tube is aligned with the other of the openings of the tubular sheath, and a pressure transducer in fluid communication with the elongated tube proximal end so that blood from the vascular structure is communicated to the pressure transducer when the elongated tube opening is aligned with one of the tubular sheath openings, thereby to directly measure the blood pressure;

wherein the blood pressure measuring device has a distal portion that is inserted into the vascular structure, and wherein an exterior surface of the distal portion of the blood pressure measuring device has a cross sectional profile of a single circle.

5. The pressure measuring device of claim 4 wherein at least one of the elongated tube or tubular sheath comprises a radiopaque marker at a distal end thereof.

* * * * *